United States Patent
Branson et al.

(10) Patent No.: US 12,285,282 B2
(45) Date of Patent: Apr. 29, 2025

(54) SYSTEM AND METHOD FOR NOTIFICATION OF IMAGING MODE OF X-RAY IMAGING SYSTEM

(71) Applicant: GE Precision Healthcare LLC, Wauwatosa, WI (US)

(72) Inventors: Michelle Branson, Harmony, PA (US); Beth Heckel, Waukesha, WI (US); Eric Hart, Muskego, WI (US); Adam Pluim, Brookfield, WI (US); Ping Xue, Pewaukee, WI (US)

(73) Assignee: GE Precision Healthcare, LLC, Wauwatosa, WI (US)

( * ) Notice: Subject to any disclaimer, the term of this patent is extended or adjusted under 35 U.S.C. 154(b) by 310 days.

(21) Appl. No.: 18/089,968

(22) Filed: Dec. 28, 2022

(65) Prior Publication Data

US 2024/0215935 A1 Jul. 4, 2024

(51) Int. Cl.
*A61B 6/00* (2024.01)
*A61B 6/42* (2024.01)

(52) U.S. Cl.
CPC .......... *A61B 6/4208* (2013.01); *A61B 6/4405* (2013.01)

(58) Field of Classification Search
CPC .... A61B 6/00; A61B 6/03; A61B 6/40; A61B 6/405; A61B 6/44; A61B 6/4411; A61B 6/4417; A61B 6/46; A61B 6/462; A61B 6/545; H05G 1/58
See application file for complete search history.

(56) References Cited

U.S. PATENT DOCUMENTS

| | | | |
|---|---|---|---|
| 6,795,526 B2 | 9/2004 | Kump et al. | |
| 2012/0128125 A1 | 5/2012 | Jabri et al. | |
| 2014/0185107 A1 | 7/2014 | Li et al. | |
| 2021/0183055 A1 | 6/2021 | Rao et al. | |

FOREIGN PATENT DOCUMENTS

| | | | |
|---|---|---|---|
| JP | 4763183 B2 | * | 8/2011 |
| JP | 2019069343 A | | 5/2019 |

* cited by examiner

*Primary Examiner* — Don K Wong
(74) *Attorney, Agent, or Firm* — Boyle Frederickson S.C

(57) ABSTRACT

According to one aspect of an exemplary embodiment of the disclosure, a system and method for providing an indication of the mode of operation of an X-ray imaging system operable in a fixed mode or an automatic optimization of parameter (AOP) mode, and an operational mode indication system including at least one of a visual indicator and an audio indicator. The selection of an operational mode for the X-ray system enables a control processing unit to activate the operational mode indication system in a first manner and in a second manner at least during the operation of the radiation source and the detector to provide an indication of a current mode of operation of the imaging system, wherein the first manner is readily discernable from the second manner.

20 Claims, 4 Drawing Sheets

SYSTEM AND METHOD FOR NOTIFICATION OF IMAGING MODE OF X-RAY IMAGING SYSTEM

FIELD OF THE DISCLOSURE

The subject matter disclosed herein generally relates to X-ray imaging systems. More specifically, the subject matter relates to systems and methods for notifying an operator of the operating condition of an X-ray imaging system.

BACKGROUND OF THE DISCLOSURE

X-ray systems, such as digital radiography (RAD) systems, mammography systems, computed tomography systems, and the like are used to generate images showing internal features of a subject. In the medical context, such systems are used for viewing internal anatomies and tissues, such as for diagnostic purposes. In modern projection X-ray systems, for example, X-rays are generated by an X-ray source and are directed towards a patient or other subject. The X-rays transfer through the subject, and are absorbed or attenuated by internal features. The resulting X-rays impact a digital detector where image data is generated. Collecting the image data allows for reconstruction of a useful image. Similar techniques are used for mammography, computed tomography, fluoroscopy and tomosynthesis image generation.

It is a general goal in radiography to acquire sufficient image data for reconstruction of a useful image, while optimizing, and often minimizing the dosage of radiation to the patient. Various techniques have been developed for estimating or controlling the imaging process to obtain these goals. The exposure parameters, e.g., peak kilovoltage and milliampere second values, that define the X-ray beam generated by the X-ray source directed towards the patient can be controlled by a computing device using, for example, automatic exposure control (AEC) methods.

In an attempt to minimize the radiation dose to a patient and consistent dose to image sensors, with regard to the operation of AEC systems and methods, a computing device controls the exposure parameters based on information received from sensors in the form of one or more dose sensors, such as ion or ionization chambers or solid-state sensors, coupled with the X-ray detector which measure radiation exposure. Current digital radiography systems using AEC or photo-timing to control exposure (and consequently dose) to the patient rely on proper alignment of patient anatomy with respect to fixed locations on the digital RAD system, i.e., the positions on the detector where the sensors/ionization chambers are located.

Problems arise, however, in situations where it is difficult to align body parts with the fixed locations on the system, especially when these fixed locations or sensors are not properly adapted to the patient anatomies, patient sizes, and so forth. Because the exposure measurement devices, such as ion chambers, serve as integrators of received radiation, misalignment of the anatomy being imaged relative to the ionization chambers/sensors may result in under or overestimating the radiation actually applied to the anatomy or region of interest (ROI).

Further, certain radiography and digital radiography (RAD) systems, such as mobile RAD systems, cannot employ AEC systems and methods due to the lack of ionization chambers associated with the detector in these mobile RAD systems.

As an alternative to either manual or AEC systems and methods for exposure optimization, the use of a preliminary low dose X-ray image, i.e., a preshot, can be utilized to determine the imaging parameters. One of advantages with preshot is the automatic identification of anatomical area or area or region of interest (ROI) in anatomy on the image from the preshot. Then, based on signal estimated from those regions of the detector in alignment with the ROI, an appropriate technique and/or imaging parameters can be set for main shot/X-ray image to achieve desired dose level and image quality for main shot image. One example of a suitable process of this type is disclosed in U.S. Pat. No. 6,795,526, entitled Automatic Exposure Control For A Digital Image Acquisition System, the entirety of which is expressly incorporated by reference herein for all purposes.

Due to time required to acquire, transfer, and process the preshot image, acquisition of preshot and main shot can often be done by users with two exposure activations. However, the use of two separate activations can affects the typical x-ray imaging workflow in which the exposure is obtained in its entirety with one press.

To overcome this obstacle concerning the use of an automatic optimization of parameter (AOP) mode with the preshot for the detecting the ROIs and providing appropriate exposure parameters with the speed necessary to accommodate an image with preshot on a RAD system, a system and method for an AOP mode of obtaining both a preshot image of the ROI to determine proper exposure parameters for use in a subsequent main shot of the ROI using a single imaging set up procedure for a RAD imaging system is disclosed in co-owned U.S. patent application Ser. No. 17/985,650, entitled System And Method For Exposure Control And Imaging Technique Optimization Employing A Preshot X-Ray Image, the entirety of which is expressly incorporated herein by reference its entirety for all purposes. With this system and method, the use of a preshot image can more than adequately supply the required exposure parameter information for use in a fixed or mobile RAD imaging system. Users will also become more efficient in delivering both dose effective and patient effective care through the quick automation and appropriate technique parameters that the preshot provides for the subsequent main shot using the RAD system.

Thus, with this improvement the RAD system can be operated in either of a fixed mode, where only a single exposure with predefined technique is obtained, or the AOP mode, where the preshot image and the main shot are each obtained within the imaging process. As both imaging modes require only a single set up, the operator of the RAD system can set up the patient to image the ROI, and can activate the RAD system by depressing the activation switch/button once to have the RAD system perform either imaging procedure.

When activating the RAD system, as a notification to the operator the RAD system provides an indication to the operator that the RAD system is performing an imaging procedure. This notification can take the form of a light source, such as that disclosed in US Patent Application Publication No. US2014/0185107, entitled Method And Device For Indicating Scanning Condition And Scanning Apparatus And Scanning System Related Thereto, the entirety of which is expressly incorporated by reference herein for all purposes, or an audible tone that is activated when the imaging procedure is being performed by the RAD imaging system.

However, when the RAD imaging system is operated in either of the fixed mode or the AOP mode, the operation notification provided by the RAD imaging system is the same. This can create issues when the operator desires to operates the RAD system in a particular manner, but cannot determine from the operation notification from the RAD system what mode is being utilized by the RAD imaging system. For example, during the operation of the RAD imaging system in AOP mode, when the operator believes the RAD imaging system is operating in fixed mode, the operator may release the activation switch after the preshot, thereby stopping any main shot from being obtained. Alternatively, even if the operator knows the RAD imaging system is operating in the AOP mode, after the preshot the operator may believe the entire imaging procedure is complete and may release the activation switch, also stopping any main shot from being obtained. In each case, the lack of indication to the operator of the current AOP mode of operation of the RAD imaging system can create unnecessary retakes for the patient, limiting the effectiveness of the exposure reduction provided by the AOP mode of operation for the RAD imaging system.

Therefore, it is desirable to develop a notification system and method for a RAD imaging system that can provide information to the operator concerning the current mode of operation of the RAD imaging system is a readily apparent and discernable manner.

SUMMARY OF THE DISCLOSURE

According to one aspect of an exemplary embodiment of the disclosure, a method for providing an indication of the mode of operation of an X-ray imaging system, includes the steps of providing an X-ray imaging system including a radiation source, a detector alignable with the radiation source, the detector having a support on or against which a subject to be imaged is adapted to be positioned, a control processing unit operably connected to the radiation source and detector to operate the radiation source and the detector in an imaging procedure in a fixed mode or an automatic optimization of parameter (AOP) mode to generate image data and process the image data from the detector to create images, an operational mode indication system disposed on the imaging system and operably connected to the control processing unit, the operation mode indication system including at least one of a visual indicator and an audio indicator, and an electronic memory storage operably connected to the control processing unit and including instructions for the operation of the operational mode indication system by the control processing unit, selecting an operational mode for the radiation source and the detector, operating the radiation source and detector to generate one or more images, and activating the operational mode indication system in a first manner and in a second manner at least during the operation of the radiation source and the detector to provide an indication of a current mode of operation of the imaging system, wherein the first manner is readily discernable from the second manner.

According to another aspect of an exemplary embodiment of the disclosure, a radiography imaging system includes a radiation source, a detector alignable with the radiation source, a control processing unit operably connected to the radiation source and detector to operate the radiation source and the detector in an imaging procedure in a fixed mode or an automatic optimization of parameter (AOP) mode to generate image data and process the image data from the detector to create images, an operational mode indication system disposed on the imaging system and operably connected to the control processing unit, the operation mode indication system including at least one of a visual indicator and an audio indicator, an electronic memory storage operably connected to the control processing unit and including instructions for the operation of the operational mode indication system by the control processing unit, and a user interface operably connected to the control processing unit to enable user input to the control processing unit, wherein the image processing circuitry is configured to activate the operational mode indication system in a first manner and in a second manner at least during the operation of the radiation source and the detector to provide an indication of a current mode of operation of the imaging system, wherein the first manner is readily discernable from the second manner.

These and other exemplary aspects, features and advantages of the invention will be made apparent from the following detailed description taken together with the drawing figures.

BRIEF DESCRIPTION OF THE DRAWINGS

These and other features, aspects, and advantages of the present invention will become better understood when the following detailed description is read with reference to the accompanying drawings that illustrate the best mode currently contemplated of practicing the present disclosure and in which like characters represent like parts throughout the drawings, wherein.

DETAILED DESCRIPTION OF THE DRAWINGS

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As used herein, "electrically coupled", "electrically connected", and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present.

Figure 1:
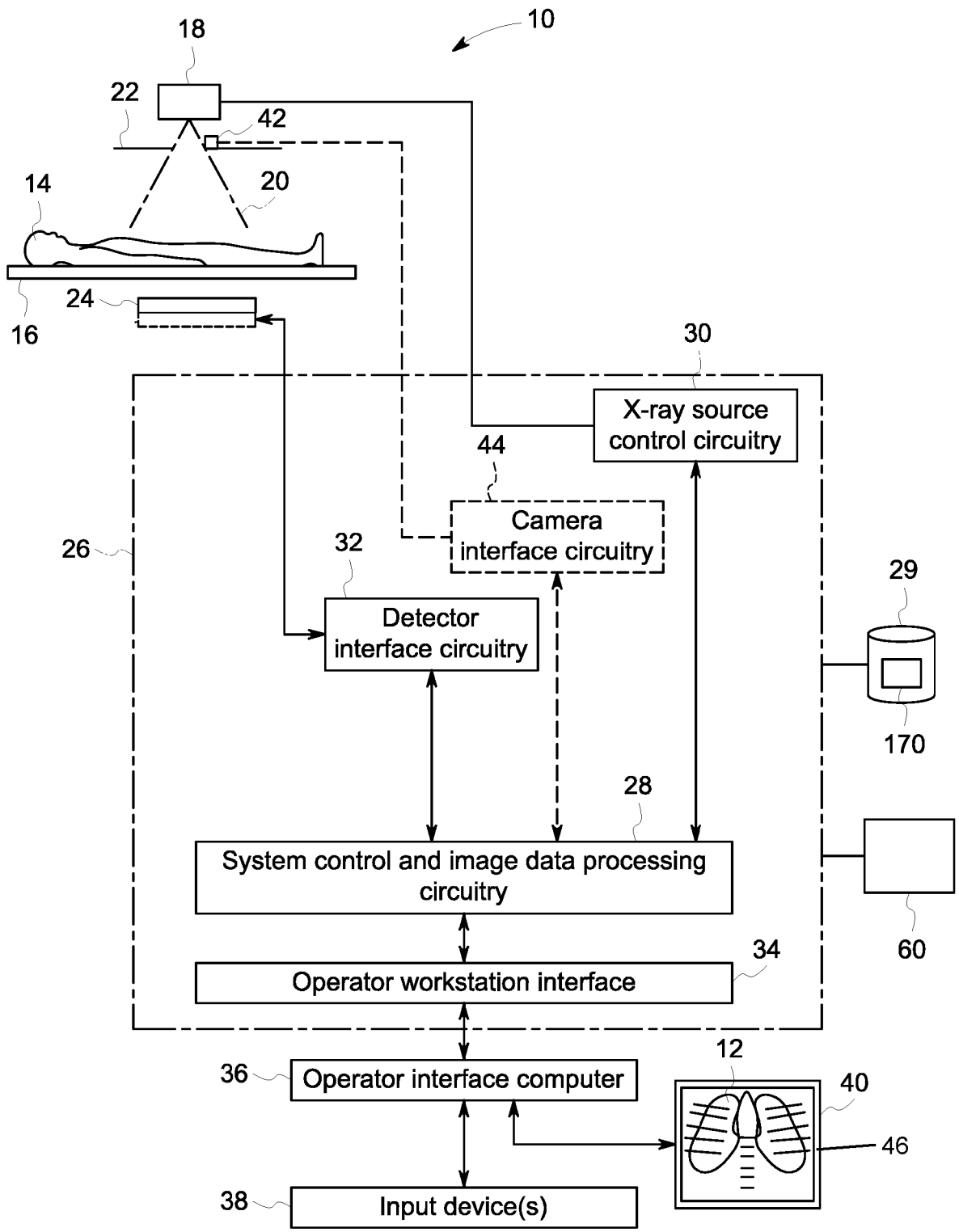
FIG. 1 is an isometric view of a radiography imaging system including an operational mode identification system, according to an exemplary embodiment of the disclosure.

Referring to FIG. 1, an X-ray imaging system 10 is illustrated that allows for identification of a region of interest (ROI) and exposure control based upon the ROI. The X-ray imaging system 10, such as that disclosed in US Patent Application Publication No. 2012/0128125, entitled Region Of Interest Determination For X-Ray Imaging, which is expressly incorporated herein by reference for all purposes, is adapted for generating images 12 of a subject 14. In a medical diagnostic context, the subject 14 may be positioned on a support 16. An X-ray source 18 is adapted to produce a beam of radiation 20 which passes through collimator 22. The radiation traverses the subject, with some of the radiation being attenuated or absorbed, and resulting radiation impacting a detector 24. Alternatively, the subject 14 can be located in a standing position in front of the detector in a digital radiography (RAD) imaging system as disclosed in US Patent Application Publication No. 2021/0183055, entitled Methods And Systems For Analyzing Diagnostic Images, which is expressly incorporated herein by reference in its entirety for all purposes.

A control processing system/processing unit/processor 26 is coupled to both the radiation source 18 and the detector 24. In general, this system 26 allows for regulation of operation of both the source 18 and the detector 24, and permits collection of information from the detector 24 for reconstruction of useful images. In the illustrated embodiment, for example, the control and processing unit/system 26 includes system control and image processing circuitry 28. Such circuitry 28 will typically include a programmed processor, supporting memory/database 29, specific applications executed by the processor during operation, which may be stored in memory/dataset 29 along with executable instructions for the operation of the control processing unit 26, and so forth. The circuitry 28 will be coupled to X-ray source control circuitry 30 that itself allows for control of operation of the X-ray source 18. The X-ray source control circuitry 30 may, for example, under the direction of the system control and image data processing circuitry 28, regulate the current and voltage applied to the X-ray source 18, alter the configuration of the collimator 20, trigger the generation of X-rays from the source 18, trigger startup and shutdown sequences of the source, and so forth.

The system control and image data processing circuitry/processing unit/processor 28 is further coupled to detector interface circuitry 32. This circuitry 32 allows for enabling the digital detector 24, and for collecting data from the digital detector 24. As will be appreciated by those skilled in the art, various designs and operations of such detectors 24 and detector interface circuitry 32 are known and are presently in use. Such designs will typically include detectors 24 having an array of discrete pixel elements defined by solid state switches and photodiodes. The impacting radiation affects the charge of the photodiodes, and the switches allow for collection of data/information regarding the impacting radiation (e.g., depletion of charge of the photodiodes). The data/information may then be processed to develop detailed images in which gray levels or other features of individual pixels in an image are indicative of the radiation impacting corresponding regions of the detector 24.

The control processing unit 26 is also illustrated as including an operator workstation interface 34. This interface allows for interaction by an operator who will typically provide inputs through an operator interface computer 36. The operator interface computer 36 and/or the system control and image data processing circuitry 28 may perform filtering functions, control functions, image reconstruction functions, and so forth. One or more input devices 38 are coupled to the operator interface computer 36, such as a keyboard, a stylus, a computer mouse, combinations thereof, among other suitable devices. The operator interface computer 36 is further coupled to a display or monitor 40 on which images may be displayed, instructions may be provided, regions of interest (ROIs) may be defined as discussed below, and so forth. In general, the operator interface computer 36 may include memory and programs sufficient for displaying the desired images, and for performing certain manipulative functions, in particular the definition of a region of interest (ROI) for image exposure control.

It should be noted that, while through the present discussion reference is made to an X-ray system 10 in the medical diagnostic context, the present invention is not so limited. For example, the invention may be used for other radiological applications, such as fluoroscopy, computed tomography, tomosynthesis and so forth. The system 10 may be used in other application contexts as well, such as part and parcel inspection, screening and so forth. Moreover, in certain contexts, and certain aspects of the detectors may be used with non-digital detectors, such as conventional film.

The system illustrated in FIG. 1 is adapted to allow for selection or definition of a region of interest (ROI) that will serve for exposure control during imaging sequences. In the particular embodiment illustrated, a camera 42 may be positioned above the patient and coupled to camera interface circuitry 44. It is contemplated that the camera 42 may be used to generate one or more images 46 of the subject 14 that can form the basis for operator definition of a region of interest (ROI) as described below. The camera 42 can have any suitable form, such as any one or more of an RGB camera, a black and white camera, a depth camera, and infrared camera, or an ultrasonic imaging camera or device. The camera interface circuitry 44 allows for triggering the camera 42 to collect a camera image data/image(s) 46 that can be processed by the camera interface circuitry 44 and forwarded to the system control and image data processing circuitry 28. The image may then be conveyed to the operator interface computer 36 and displayed on the monitor 40, optionally in conjunction with x-ray image 12.

Figure 2:
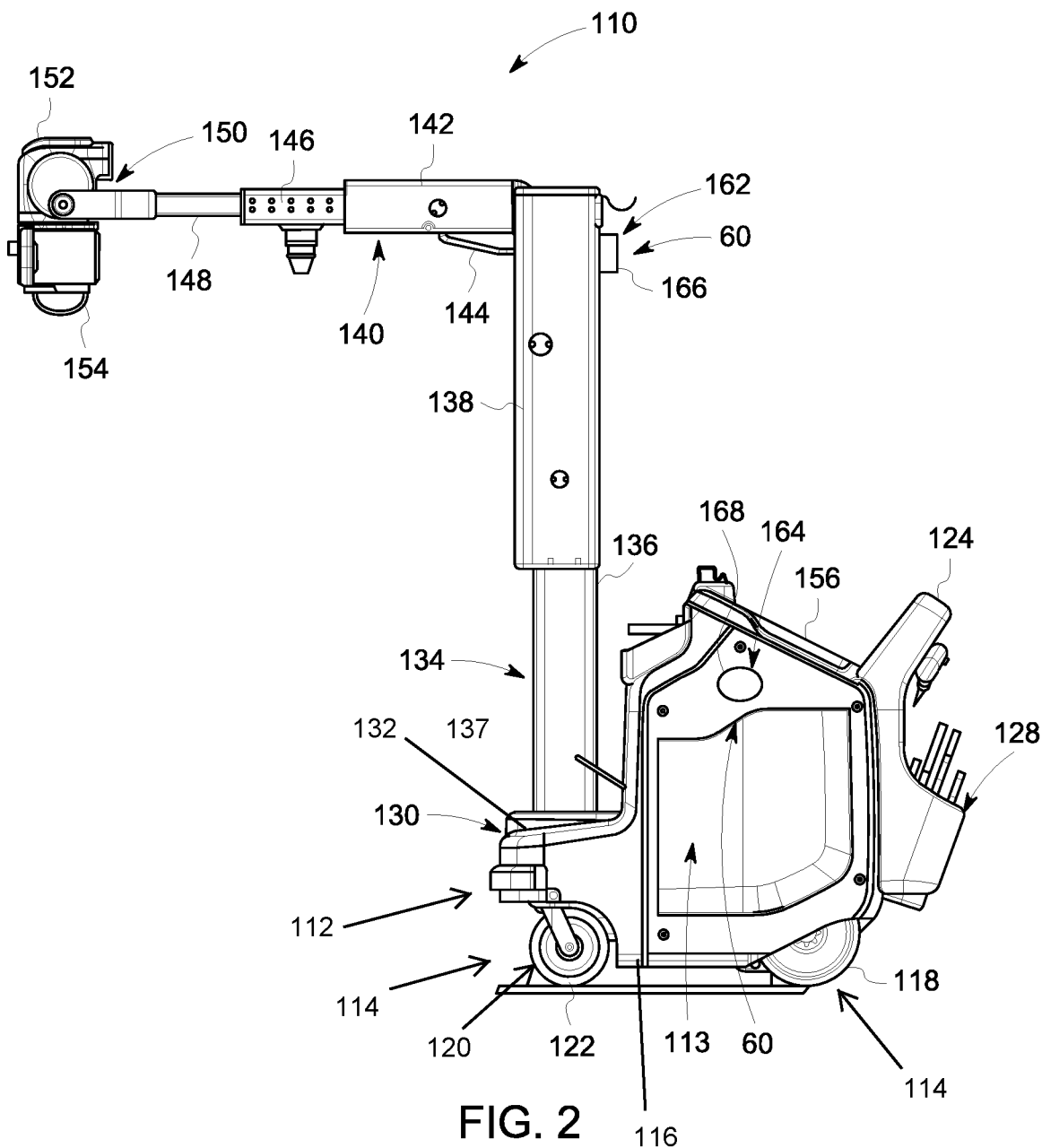
FIG. 2 is an isometric view of a mobile x-ray device including an operational mode identification system, according to an exemplary embodiment of the disclosure.

In FIG. 2, an exemplary embodiment is illustrated of a mobile x-ray device 110 constructed according to the disclosure and similar to that disclosed in U.S. Pat. No. 9,521,984, the entirety of which is hereby expressly incorporated by reference for all purposes. The mobile x-ray device 110 includes a chassis 112 that defines a body 113 including a number of wheels 114 attached to a lower surface 116 of the body 113 in order to allow the mobile x-ray device 110 to be moved over a surface by a technician. The wheels 114 can include a pair of large support wheels 118 located on an axle (not shown) directly secured to the chassis 112, and one or more directional wheels 120 affixed to the chassis 112 in a pivotal manner, such as casters 122, to facilitate the movement of the chassis 112 in a desired direction. The chassis 112 can additionally include a handle 124 extending outwardly from the chassis 112 and graspable by a technician in order to manually direct the movement of the chassis 112 where desired. In an alternative embodiment or as an addition to the above embodiment, the chassis 112 may include a suitable motor (not shown) that is operably connected to the wheels 114, such as to the support wheels 118, in order to provide motorized movement capability to the chassis 112.

The body 113 of the chassis 112 defines a large rear end 128 and a tapered, narrow front end 130. Within the rear end 128 the body 113 encloses a number of operative systems (not shown) for the mobile x-ray device 110 such as the operative systems for the processing of x-ray data to provide x-ray images using the x-ray device 110. The narrow front end 130 defies a platform 132 that supports a telescopic column 134 that can be moved as desired to position an x-ray emitter 136 attached to the column 134 where necessary to obtain the x-ray images.

The telescopic column 134 includes a lower fixed portion 136 disposed on the platform 132, where the lower portion 136 is attached to the platform 132 by a suitable rotation mechanism (not shown) by a rotational collar 137 secured to the fixed portion 136 and rotatable with respect to the platform 132, that enables the lower portion 136 to rotate with regard to the platform 132 along a vertical axis extending upwardly from the platform 132 through the lower portion 136.

The column 134 additionally includes an upper telescopic portion 138 that is moveably attached to the lower fixed portion 136. Opposite the lower fixed portion 136, the upper telescopic portion 138 supports a telescoping arm 140. The telescoping arm 140 is movable vertically with regard to the telescopic portion 138. The telescoping arm 140 includes a fixed section 142 secured to a carriage 144 that is movably disposed on the telescopic portion 38. A number of independently moveable sections 146,148 are secured to the fixed section 144 and can be selectively moved in a horizontal direction with regard to the fixed section 144 and one another to extend and retract the telescoping arm 140 relative to the telescopic portion 138.

Opposite the telescoping portion 138 the telescoping arm 140 supports a head assembly 150 on the outermost moveable section 148. In illustrated exemplary embodiment of FIG. 2, the head assembly 150 includes an x-ray source or emitter 152 and a collimator 154, and is secured to the moveable section 148 in any suitable manner that enables the head assembly 150 to pivot and/or rotate relative to the moveable section 148 in order to position the emitter 152 where necessary to obtain the desired x-ray images.

The various components of the telescopic column 132, i.e., the fixed portion 136 and the telescopic portion 138, and the telescoping arm 140, i.e., the fixed section 144 and the moveable sections 146,148, are each formed of a material that is sufficiently rigid to support the various components of the x-ray device 110 that are attached thereto, while also be able to be formed with a hollow interior to enable various wiring and other operational connections between body 113 and the emitter 152, such as through an aperture (not shown) in the platform 132 beneath the column 134, for the operation of the x-ray device 110 to be made completely within the interior of the x-ray device 110.

The mobile x-ray device 110 additionally includes a user console 156 on the body 113 in front of the handle 124 for the display of x-ray images obtained by the x-ray device 110 and/or for the operational control of the emitter 152 to obtain the x-ray images. The console 156, e.g., in the form of a touchscreen, is one exemplary embodiment of the form of the user interface 38 and/or display 40 that is operably connected to the operator interface computer 36 to enable control of the control processing unit 26 for the desired manner and/or mode of operation of the X-ray system 10.

Figure 3:
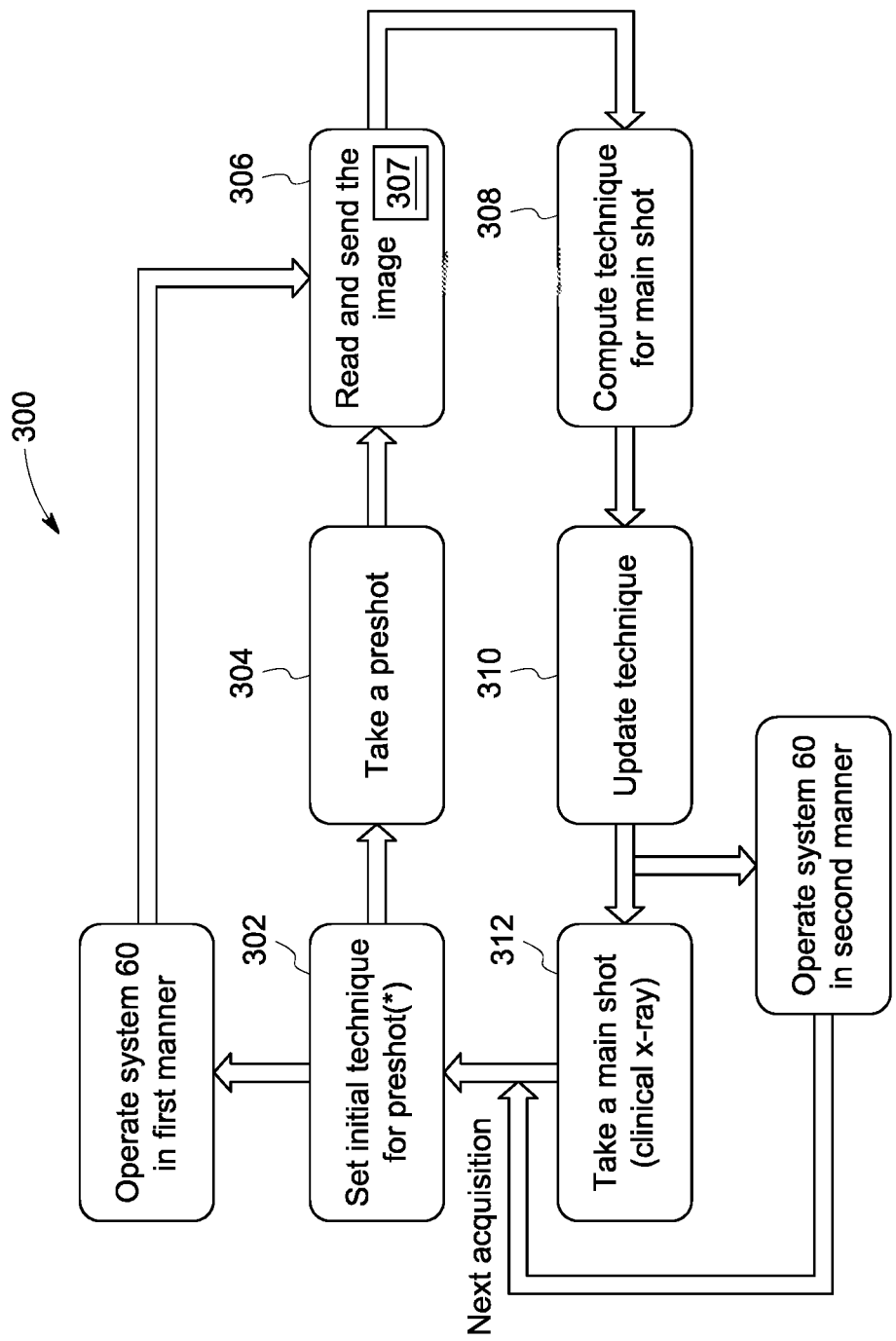
FIG. 3 is a flowchart illustrating the operation of the imaging system and operational mode identification system in an AOP mode, according to an exemplary embodiment of the disclosure.

FIG. 3 schematically illustrates the method 300 employed to obtain the exposure parameters for an image pasting procedure performed using the system 10. In an initial step 302, the system 10 sets an exposure parameter or technique for obtaining one or more preshots of the subject 14, with the radiation dose from the one or more preshots being equivalent to or less than the dose from system employing prior art AEC systems. In step 304, the one or more preshots are taken using the predetermined techniques, and in step 306 the image data from the detector 24 is transmitted to and read by the image data processing circuitry 28 with an optional step 307 to determine or locate the position of any ROI(s) within the preshots. In step 308, the image data processing circuitry 28 determines an updated technique/ exposure parameters optimized for the ROI(s) for the main shot image(s) corresponding to each of the preshots.

Additionally, the steps 304-308 can be performed individually for each preshot to be obtained, or can be performed collectively, e.g., all preshots being taken in step 304 prior to sending the image data to the image data processing circuitry 28 in step 306.

After determination of the updated technique/exposure parameters optimized for the ROI(s), the image data processing circuitry 28 outputs this updated technique to the control and processing system 26 in step 310. This updated technique/exposure parameters are then employed by the control and processing system 26 in step 312 to obtain the main shot image(s). After obtaining the main shot image(s) in step 312, the method 300 can terminate, or can reset to step 302 to prepare to obtain another set of one or more preshots.

With regard to the steps 308 and 310 of the method 300, after the determination of the location and form, e.g., shape and thickness, of the ROIs in the preshot images, the image data processing circuitry 28 can optimize the parameters and/or technique for the main shot images to be taken corresponding to the preshot images including each of the ROIs. The optimization of the parameters and technique based on the data from the preshot images can include, but is not limited to kVp, mA, ms, filter, and the FOV for each corresponding main shot, with the image data processing circuitry 28 configured to automatically adjust any one or more of these parameters.

Additionally, separate from the method 300 in FIG. 3, the system 10 can be operated in a fixed or manual mode where the X-ray source 18/emitter 152 can be operated in a continuous manner for a duration selected by the operator and/or by the control processing unit 26 in order to obtain an image of the subject 14.

Figure 4:
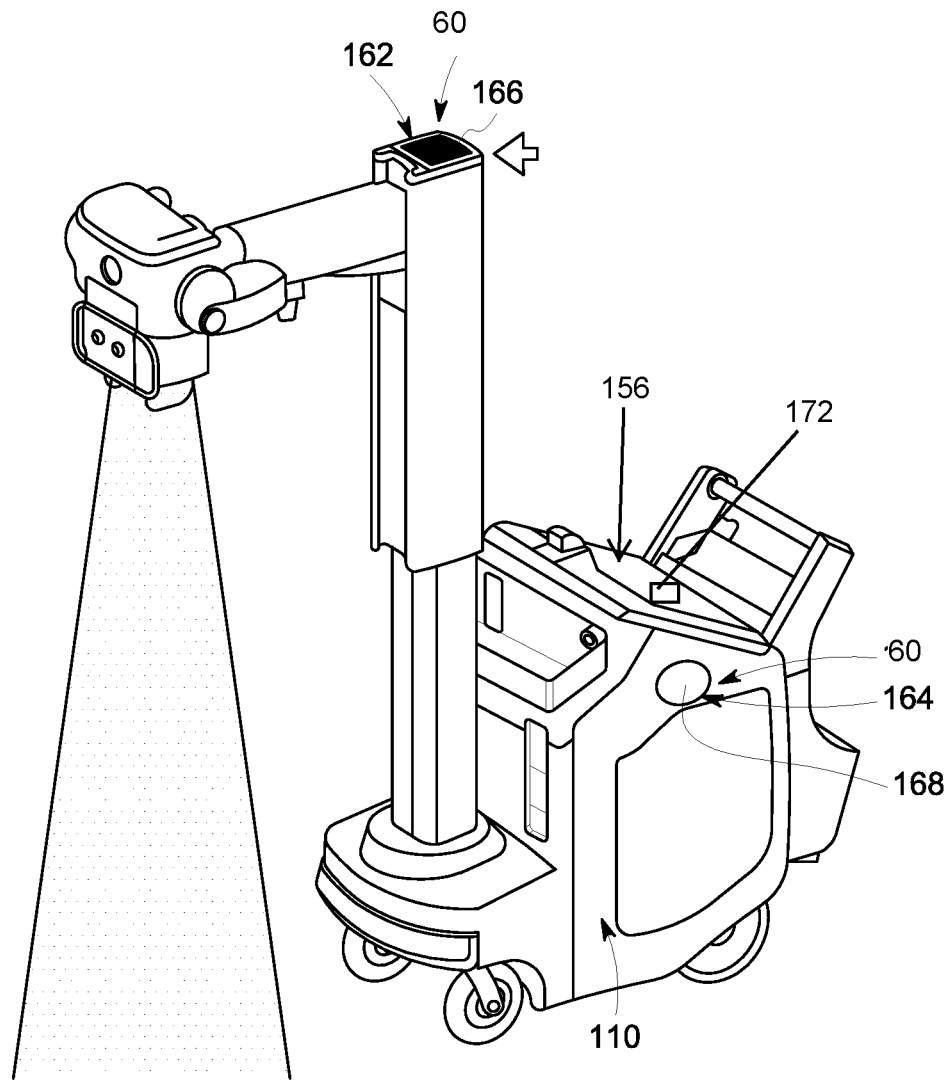
FIG. 4 is an isometric view of the mobile x-ray device of FIG. 2, according to an exemplary embodiment of the disclosure.

Referring now to FIGS. 1, 3 and 4, during the operation of the system 10 to obtain the image, the control processing unit 26 is provided with an instruction regarding the mode of operation of the X-ray system 10 that is desired or selected either automatically by the system 10,110, such as in response to certain parameters specified for the imaging procedure to be performed, or manually by the operator, i.e., a fixed mode or an AOP mode. With this information, the control processing unit 26 is configured to operate an operational mode notification system 60 disposed on the X-ray system 10 and operably connected to the control processing unit 26. In operating the notification system 60, the control processing unit 26 utilizes the input information regarding the desired mode of operation to provide an indication to the operator of the mode of operation of the X-ray system 10 when the X-ray system 20 is in operation, as well as to provide an indication of any changes in the operational state of the X-ray system 10 while the X-ray system 10 is in operation.

In one exemplary embodiment of the operational mode notification system 60, as best shown in FIGS. 1 and 4, the notification system 60 includes a visual indicator 162 and an audio indicator 164. The visual indicator 162 is mounted in a readily visible location on the exterior of the X-ray system 10,110, such as on the telescopic column 134. In alternative embodiments, the system 60 can additionally include corresponding indicators 172 located on the console 156, such as in the form of electronic icons presented on the console 156, that operate in conjunction with the visual indicator 162 (e.g., using the same colors as the visual indicator 162) and/or the audio indicator 164 (e.g., providing a written indication of the mode) to provide indications on the console 156 in addition to and/or as a substitute for one or both of the visual indicator 162 and/or the audio indicator 164 to indicate the mode of operation of the x-ray system 10,110. In an exemplary embodiment, while being able to have any suitable form for a visual indication, the visual indicator 162 is formed a light source 166, such as one or more light emitting diodes (LEDs), capable of being operated by the control processing unit 26 to emit visible light of various colors and/or patterns from the light source 166.

The audio indicator 164 is also disposed at least partially on an exterior portion of the X-ray system 10,110 where sound(s) emitted from the audio indicator 164 is/are readily heard by an operator of the X-ray system 10,110, such as on the body 113 around the console 156. The audio indicator 164 can have any suitable form for emitting sound therefrom under the control of the control processing unit 26, and in one exemplary embodiment takes the form of a speaker 168.

In operation, the information provided either from the system 10,110 or from the user input 38/console 156 to the control processing unit 26 regarding the particular desired mode of operation for the X-ray system 10 enables the control processing unit 26 to access instructions 170 for the corresponding operation of the operational mode notification system 60, which can be electronically stored in memory 29 or in any other suitable non-transitory electronic storage location, database or memory. The instructions 170 retained in the memory 29 provide the control processing unit 29 with the duration(s), brightness, color(s) and/or pattern(s) of light to be generated and emitted from the visual indicator 162/light source 166 during the operation of the X-ray system 10,110 in the selected operational mode. The instructions 170 can also provide the control processing unit 26 with the duration(s), tone(s) and/or pattern(s) of sound to be generated and emitted from the audio indicator 164/speaker 168 during the operation of the X-ray system 10,110 in the selected operational mode.

Figure 5:
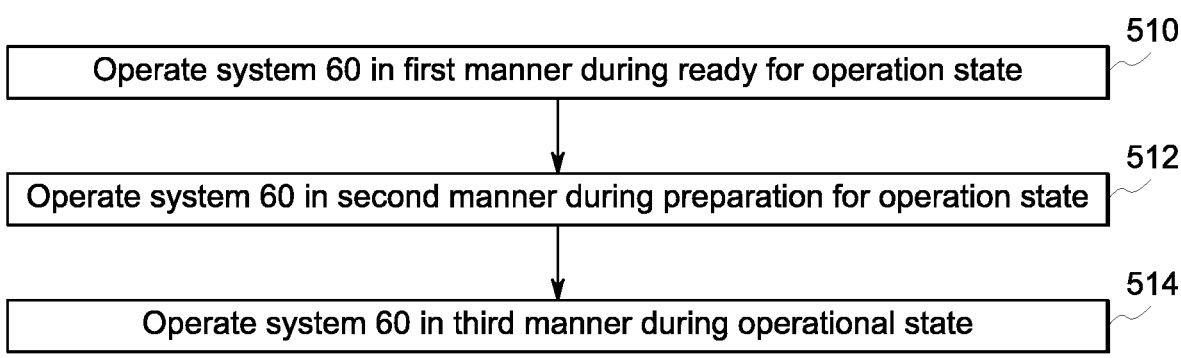
FIG. 5 is a flowchart illustrating the operation of the imaging system and operational mode identification system in a fixed mode, according to an exemplary embodiment of the disclosure.

In an exemplary embodiment, when the system 10,110 automatically selects or the operator selects via the user interface 38/console 156 to operate the X-ray system 10,110 in a fixed mode, the accessed instructions 170 can instruct the control processing unit 26 to operate the visual indicator 162/light source 166 and the audio indicator 164/speaker 168 in a constant manner for the entire duration of the operation of the X-ray system 10,110 in a fixed mode. The use of a constant manner of operation of the visual indicator 162/light source 166 and the audio indicator 164/speaker 168 during the fixed mode can readily correspond to and identify the fixed mode of operation to the operator. As shown in FIG. 5, the method 500 illustrating the operation of the X-ray system 10,110 in fixed mode includes step 501 of operating the visual indicator 162/light source 166 and the audio indicator 164/speaker 168 in a fixed manner during the duration of the fixed mode, i.e., step 502.

Alternatively, when the system 10,110 automatically selects or the operator selects via the user interface 38/console 156 to operate the X-ray system 10,110 in an AOP mode, the accessed instructions 170 can instruct the control processing unit 26 to operate the visual indicator 162/light source 166 and the audio indicator 164/speaker 168 in different manners at different times during the AOP mode of operation. More specifically, the control processing unit 26 can operate the visual indicator 162/light source 166 and the audio indicator 164/speaker 168 in a first manner during the preshot period and in a second manner during the main shot period. With the readily discernable changes in the operation of the visual indicator 162/light source 166 and the audio indicator 164/speaker 168 by the control processing unit 26 during the preshot period and main shot period, e.g., changes in the duration(s), brightness, color(s), tone(s) and/or pattern(s) of the light and/or sound being emitted, the varying manner of operation of the visual indicator 162/light source 166 and the audio indicator 164/speaker 168 during the AOP mode can readily correspond to and identify the AOP mode of operation to the operator. As shown in the illustrated exemplary embodiment of FIG. 3, the method 300 illustrating the operation of the X-ray system 10,110 in AOP mode includes step 303 of operating the visual indicator 162/light source 166 and the audio indicator 164/speaker 168 in a first manner during the duration of the preshot period, i.e., step 304, and step 311 of operating the visual indicator 162/light source 166 and the audio indicator 164/speaker 168 in a second manner during the duration of the main shot period, i.e., step 310. The first manner and the second manner include indications from the visual indicator 162/light source 166 and the audio indicator 164/speaker 168 that are readily discernable from one another, such that the operator is easily informed of the performance and duration of the preshot period and the main shot period during the AOP mode of operation.

In another exemplary embodiment, as the operation of the X-ray system 10,110 in the fixed mode and in the main shot period of the AOP mode correspond to one another, the operation of the visual indicator 162/light source 166 and the audio indicator 164/speaker 168 by the control processing unit 26 during the fixed mode and the main shot period of the AOP mode can correspond to one another, further conveying to the operator the type of imaging process that is currently being performed by the X-ray system 10,110.

In alternative exemplary embodiments of the disclosure, the instruction 170 and manner of operation of the visual indicator 162/light source 166 and/or the audio indicator 164/speaker 168 by the control processing unit 26 can include additional separate manners of operation for additional steps of operation of each mode, including notifications for the period leading up to and/or following the actual operation of the X-ray system 10,110 in either mode, among others. For example, with reference to FIG. 5, in either mode of operation, the control processing unit 26 can operate the visual indicator 162/light source 166 in step 510 to emit light of a first color, pattern and/or intensity, e.g., a steady green light, when the X-ray system 10 is ready for operation, in step 512 to emit light of a second color, pattern and/or intensity, e.g., a flashing green light, when the X-ray system 10 is in preparation for operation, and in step 514 to emit light of a third color, pattern and/or intensity, e.g., a steady yellow or red light, when the X-ray system 10 is in operation, e.g., when the operator is pressing the activation switch. Further, each of the first light, second light and third light can be accompanied by a first sound, second sound and third sound, respectively, emitted by the audio indicator 164/speaker 168 as operated by the control processing unit 26 that audibly reinforces the indication provided by the first light, second light and third light, e.g., a soft intermittent beep for the first sound, a louder and/or faster intermittent beep for the second sound, and a louder and/or steady tone for the third sound. In addition, after operation of the X-ray system 10 in either mode, the visual indicator 162/light source 166 and the audio indicator 164/speaker 168 can be operated by the control processing unit 26 in a reverse order, or any other suitable manner to provide an indication of the termination of the operation of the X-ray system 10 in the selected mode.

Thus, with the ability of the operational mode indication system 60 to be operated by the control processing unit 26 in a manner corresponding to the particular mode of operation of the X-ray system 10,110, i.e., fixed or AOP, the operator is provided with a readily discernable indication of the current mode of operation of the X-ray system 10,110, as well as optionally an indication of the step of the current mode/imaging process in which the X-ray system 10,110 is currently operating, which minimizes inadvertent stoppages in the operation of the X-ray imaging system 10,110 and the consequent need for retakes of the desired X-ray images.

Finally, it is also to be understood that the system 10 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system may include at least one processor and system memory/data storage structures, which may include random access memory (RAM) and read-only memory (ROM). The at least one processor of the system 10 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application and/or artificial intelligence (AI) that adapts the controller to perform the methods disclosed herein may be read into a main memory of the at least one processor from a computer-readable medium. The term "computer-readable medium", as used herein, refers to any medium that provides or participates in providing instructions to the at least one processor of the system 10 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is understood that the aforementioned compositions, apparatuses and methods of this disclosure are not limited to the particular embodiments and methodology, as these may vary. It is also understood that the terminology used herein is for the purpose of describing particular exemplary embodiments only, and is not intended to limit the scope of the present disclosure which will be limited only by the appended claims.

We claim:

1. A method for providing an indication of the mode of operation of an X-ray imaging system, the method comprising the steps of:
   a. providing an X-ray imaging system comprising:
      i. a radiation source;
      ii. a detector alignable with the radiation source, the detector having a support on or against which a subject to be imaged is adapted to be positioned;
      iii. a control processing unit operably connected to the radiation source and detector to operate the radiation source and the detector in an imaging procedure in a fixed mode or an automatic optimization of parameter (AOP) mode to generate image data and process the image data from the detector to create images;
      iv. an operational mode indication system disposed on the imaging system and operably connected to the control processing unit, the operation mode indication system including at least one of a visual indicator and an audio indicator; and
      v. an electronic memory storage operably connected to the control processing unit and including instructions for the operation of the operational mode indication system by the control processing unit;
   b. selecting an operational mode for the radiation source and the detector;
   c. operating the radiation source and detector to generate one or more images; and
   d. activating the operational mode indication system in a first manner and in a second manner at least during the operation of the radiation source and the detector to provide an indication of a current mode of operation of the imaging system, wherein the first manner is readily discernable from the second manner.

2. The method of claim 1, wherein the step of selecting an operational mode comprises selecting an automatic optimization of parameter (AOP) operational mode, and wherein the step of activating the operational mode indication system in a first manner and in a second manner comprises:
   a. activating the operational mode indication system in the first manner during a preshot period of operation of the radiation source and the detector; and
   b. activating the operational mode indication system in the second manner during a main shot period of operation of the radiation source and the detector.

3. The method of claim 2, wherein the visual indicator is a light source and wherein the steps of activating the operational mode indication system in a first manner and in a second manner comprises:

a. activating the light source to emit a first light during the preshot period of operation of the radiation source and the detector; and
b. activating the light source to emit a second light during the main shot period of operation of the radiation source and the detector.

4. The method of claim 3, wherein the first light and the second light differ in color from one another.

5. The method of claim 3, wherein the first light and the second light differ in brightness from one another.

6. The method of claim 3, wherein the first light and the second light differ in pattern from one another.

7. The method of claim 2, wherein the audio indicator is a speaker and wherein the steps of activating the operational mode indication system in a first manner and in a second manner comprises:
a. activating the speaker to emit a first sound during the preshot period of operation of the radiation source and the detector; and
b. activating the speaker to emit a second sound during the main shot period of operation of the radiation source and the detector.

8. The method of claim 7, wherein the first sound and the second sound differ in tone from one another.

9. The method of claim 7, wherein the first sound and the second sound differ in volume from one another.

10. The method of claim 7, wherein the first sound and the second sound differ in pattern from one another.

11. The method of claim 2, wherein the operational mode notification system includes both a visual indicator and an audio indication and wherein the steps of activating the operational mode indication system in a first manner and in a second manner comprises:
a. activating the operational mode notification system to emit a first light and a first sound during the preshot period of operation of the radiation source and the detector; and
b. activating the operational mode notification system to emit a second light and a second sound during the main shot period of operation of the radiation source and the detector.

12. The method of claim 2, further comprising the step of activating the operational mode identification system in a third manner prior to the preshot period of operation of the radiation source and the detector, wherein the third manner is readily discernable from each of the first manner and the second manner.

13. The method of claim 1, wherein the step of selecting an operational mode comprises selecting a fixed operational mode, and wherein the step of activating the operational mode indication system in a first manner and in a second manner comprises:
a. activating the operational mode indication system in the first manner prior to the operation of the radiation source and the detector; and
b. activating the operational mode indication system in the second manner during the operation of the radiation source and the detector.

14. The method of claim 13, wherein the visual indicator is a light source and wherein the steps of operating the operational mode indication system in a first manner and in a second manner comprises:
a. activating the light source to emit a first light prior to the operation of the radiation source and the detector; and
b. activating the light source to emit a second light during the operation of the radiation source and the detector.

15. The method of claim 13, wherein the audio indicator is a speaker and wherein the steps of operating the operational mode indication system in a first manner and in a second manner comprises:
a. activating the speaker to emit a first sound prior to the operation of the radiation source and the detector; and
b. activating the speaker to emit a second sound during the operation of the radiation source and the detector.

16. The method of claim 1, wherein the X-ray imaging system includes a user interface operably connected to the control processing unit to enable user input to the control processing unit, and wherein the step of selecting an operational mode for the radiation source and the detector comprises selecting the operational mode via the user interface.

17. A radiography imaging system comprising:
a. a radiation source;
b. a detector alignable with the radiation source;
c. a control processing unit operably connected to the radiation source and detector to operate the radiation source and the detector in an imaging procedure in a fixed mode or an automatic optimization of parameter (AOP) mode to generate image data and process the image data from the detector to create images;
d. an operational mode indication system disposed on the imaging system and operably connected to the control processing unit, the operation mode indication system including at least one of a visual indicator and an audio indicator;
e. an electronic memory storage operably connected to the control processing unit and including instructions for the operation of the operational mode indication system by the control processing unit;
f. a user interface operably connected to the control processing unit to enable user input to the control processing unit;
wherein the image processing circuitry is configured to activate the operational mode indication system in a first manner and in a second manner at least during the operation of the radiation source and the detector to provide an indication of a current mode of operation of the imaging system, wherein the first manner is readily discernable from the second manner.

18. The radiography imaging system of claim 17, wherein the radiation source and detector are operable in an automatic optimization of parameter (AOP) operational mode, and wherein the control processing unit is configured to activate the operational mode indication system in the first manner during a preshot period of operation of the radiation source and the detector and to activate the operational mode indication system in the second manner during a main shot period of operation of the radiation source and the detector.

19. The radiography imaging system of claim 18, wherein the operational mode notification system includes both a visual indicator and an audio indication and wherein the control processing unit is configured to activate the operational mode indication system to emit a first light and a first sound during the preshot period of operation of the radiation source and the detector and to emit a second light and a second sound during the main shot period of operation of the radiation source and the detector.

20. The radiography imaging system of claim 17, wherein the radiation source and detector are operable in a fixed operational mode, and wherein the control processing unit is configured to activate the operational mode indication system in the first manner prior to operation of the radiation source and the detector and to activate the operational mode indication system in the second manner during operation of the radiation source and the detector.

* * * * *